United States Patent [19]
Stahly

[11] 4,329,359
[45] May 11, 1982

[54] METHOD FOR IMPROVING THE METABOLIC STABILITY AND SURVIVAL OF NEWBORN PIGS

[75] Inventor: Tim S. Stahly, Lexington, Ky.

[73] Assignee: University of Kentucky Research Foundation, Lexington, Ky.

[21] Appl. No.: 107,886

[22] Filed: Dec. 28, 1979

[51] Int. Cl.³ .................. A61K 31/23; A61K 31/22; A61K 31/045
[52] U.S. Cl. ............................ 424/312; 424/314; 424/343
[58] Field of Search ............... 424/343, 312, 314, 313

[56] References Cited

PUBLICATIONS

Friend–J. of Animal Science, vol. 39, Oct.–Dec. 1974, pp. 1073–1077 and 1080–1081.
Seerley et al.–J. of Animal Science, vol. 38, No. 1, (1974), pp. 64–70.
Madison et al.–J. Clin. Inv., vol. 43, No. 3, (1964), pp. 408–414.
Newport et al.–Brit. J. Nutrit., vol. 41, (1979), pp. 85–93.
Allee et al.–Pro. Soc. Exp. Biol. Med., vol. 134, (1972), pp. 422–427.
Holt.–Prog. In Gastroenterology, vol. 1, (1968), pp. 277–295.
Scheig–Medium Chain Triglycerides, (1968), pp. 39–46.
Isselbacher–Medium Chain Triglycerides, (1968), pp. 21–33.

*Primary Examiner*—Sam Rosen
*Attorney, Agent, or Firm*—Birch, Stewart, Kolasch & Birch

[57] ABSTRACT

The disclosed invention concerns improving the metabolic stability of newborn pigs and increasing their survival rate by administering to a pregnant sow during its late stages of gestation an effective amount of a material selected from the group consisting of a dihydroxy alkanol having 3 to 10 carbon atoms, a triglyceride of glycerol and fatty acids containing 8 to 12 carbon atoms and the mono-and diol esters of said alkanols and said fatty acids.

6 Claims, No Drawings

METHOD FOR IMPROVING THE METABOLIC STABILITY AND SURVIVAL OF NEWBORN PIGS

BACKGROUND AND SUMMARY OF THE INVENTION

The present invention relates to an improved method for increasing the survival rate of baby pigs. More particularly, the present invention is directed to a method of increasing the survival rate of baby pigs by using a food supplement in the diet of a pregnant pig.

The low survival rate observed in baby pigs, e.g., 20 to 30% mortality between birth and weaning, is attributed largely to two factors:

(1) the high degree of metabolic immaturity in the newborn pig and (2) an insufficient energy intake by the pig in its first 2 or 3 days of life.

The magnitude of this loss can be emphasized by the fact that each 1% improvement in pig survival will generate an additional $4.00 to $7.00 profit per litter.

The major metabolic defects observed in the newborn pig are summarized as follows:

1. A low level of phosphorylase potentially decreases the rate of production of glucose from glycogen stores;

2. A defective gluconeogenic capacity limits the supply of glucose available to animals exposed to stress;

3. A deficient hepatic mitochondria number limits the use of carbohydrates as well as fatty acids for energy production;

4. A small amount of body fat impairs both thermoinsulation and the quantitative contribution of fat as a major energy source; and 5. A defective amino metabolism tends to limit a source of substrate (carbon skeletons) for gluconeogenesis.

More specifically, the high mortality rate observed in pigs is attributed largely to the newborn pigs impaired thermostability and defective gluconeogenic capacity and its inability to obtain a sufficient energy intake from the sow's milk during its first 2 or 3 days of life. Because of these major metabolic defects, as well as the others set forth hereinabove, particularly its low gluconeogenic capacity, the neonatal pig rapidly develops hypoglycemia after birth if not permitted to suckle or if subject to cold stress.

This rapid onset of hypoglycemia in the newborn pig is the result of 95% of the pig's energy reserves in the form of glycogen being used within the first 72 hours of birth regardless of whether the pig is suckled or not by the sow. The significance of the baby pig's susceptibility to hypoglycemia is indicated by the 30 to 50% death loss observed within 72 hours after birth when baby pigs are fasted from birth or when baby pigs are fed for 6 hours after birth and then fasted.

Research has been conducted to identify factors which would reduce baby pig mortality. These investigations have suggested that the existence of physiological conditions, i.e., diabetes, starvation, high dietary fat intake, etc., which are associated with elevated blood ketone levels in the sow, may result in heavier, more metabolically stable pigs at birth.

Accordingly, an object of the present invention is to provide an improved method for increasing the survival rate of baby pigs.

A further object of the present invention is to provide a method for improving the metabolic stability of the newborn pig by preventing the development of hypoglycemia in the neonatal pig shortly after birth.

Still another object of the present invention is to provide a food supplement which is effective in elevating the ketone levels in blood of the pregnant pig.

Other subjects and further scope of applicability of the present invention is to provide a food supplement which is effective in elevating the ketone levels in blood of the pregnant pig.

Other objects and further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Pursuant to the present invention, it has been found that the administration of specific alcohols and glycerides to female pigs during late stages of gestation effectively increases the liver glycogen stores in the pig at birth and prolongs the availability of the liver glycogen stores in the newborn pig. This increased availability of glycogen delays the onset of hypoglycemia in the pig and increases the survival rate (percent of pigs born alive that survive to weaning) of neonatal pigs.

The alcohols which can be used according to the present invention include dihydroxy alkanols having 3 to 10 carbon atoms and the mono- and diesters of such diols and fatty acids containing 8–12 carbon atoms, such as for example, 1,3-butanediol monooctanoate. The preferred alkanol is 1,3-butanediol.

The glycerides which can be used in the present invention include the medium chain length triglycerides such as for example the reaction product of glycerol and fatty acids containing 8 to 12 carbon atoms.

The alkanols and the glycerides are administered to the pregnant pig as a food supplement, for example, as an addition to a corn-soybean meal diet. The alkanol supplement, for example, 1,3-Butanediol, which is a ketone former, has been found to be palatable and efficiently utilized by the pig when included as a food supplement to provide about .6 to 20% of the dietary energy in the pigs diet as shown in the following table:

TABLE 2

| 1,3-Butanediol Supplementation in Growing Swine. | | | | | | |
|---|---|---|---|---|---|---|
| | 1,3-Butanediol, % of dietary energy | | | | | |
| Trait | 0 | 8 | 17 | 25 | 33 | 42 |
| Wt. gain, kg | 19.5 | 20.5 | 21.4 | 11.9 | 4.3 | 1.1 |
| ME intake, Mcal | 197 | 212 | 219 | 157 | 85 | 77 |
| ME/wt gain, Mcal/kg | 10.1 | 10.3 | 10.2 | 13.2 | 19.8 | 70.0 |
| Plasma B-hydroxybutyrate, nmole/ml | 159 | 415 | 457 | 425 | 831 | 980 |
| Acetoacetate, nmole/ml | 69 | 100 | 115 | 183 | 150 | 198 |
| Glucose, mg/dl | 75 | 72 | 95 | 97 | 142 | 119 |

As can be seen from the table, higher dietary levels of 1,3-Butanediol, e.g., greater than 25% of the dietary energy, tend to depress feed consumption and subsequent growth.

Because ketones have shown to be readily transferred across the placenta, 1,3-Butanediol, a ketone former, represents a potential 'supplemental' energy source for the developing fetus.

According to the present invention, it has been found that a short-term administration of 1,3-Butanediol in sows during late gestation results in an increased liver glycogen content in the newborn pig and an improved pig survival from birth to weaning. Advantageously, the administration of the specific food additive of the present invention can begin about 4 to 12 days, advantageously about 9 days, before parturition and continue until parturition. After parturition, the sows are allowed to consume a standard lactation diet.

The following example is provided as being exemplary of the present invention and should not be considered as being limitative of the present invention.

EXAMPLE

Sixty-eight sows were fed isocaloric intakes (6000 kcal of metabolizable energy/sow/day) of a fortified corn-soybean meal diet plus an additional 1600 kcal of metabolizable energy in the form of starch or 1,3-Butanediol beginning approximately 8 days before parturition. After parturition, all sows were allowed to consume a standard lactation diet ad libitum. The results are shown in the following table:

TABLE 3

1,3-Butanediol Supplementation in Sows During Late Gestation.[a]

| Trait | Prepartum Treatment[a] | | Change |
|---|---|---|---|
| | Control | 1,3-butanediol | |
| Pigs/litter | | | |
| At birth | 10.39 | 10.14 | |
| At weaning | 8.79 | 9.28 | +.49 |
| Avg. Pig Wt. (kg) | | | |
| At birth | 1.20 | 1.26 | +.06 |
| At weaning | 3.51 | 3.58 | +.08 |
| Pig Survival, % | 85.30 | 92.00 | +6.7 |
| Liver Glycogen, % | 11.10 | 16.20 | +5.1 |

[a]Thirty-eight and 40 litters represented in the control and 1,3-butanediol treatments, respectively.

As can be seen from the above table, the 1,3-Butanediol supplementation did not influence the number of live pigs born/litter (10.14 vs 10.39) or the average pig weights (g) at birth (1,259 vs 1,205) or at weaning (3575 vs 3510) compared to those of litters from sows fed starch. However, 1,3-Butanediol supplementation did increase liver glycogen levels in the newborn pig (16.2 vs 11.1%) and did increase the total number of pigs weaned/litter (9.28 vs 8.79) and the percent of pigs born alive (92.0 vs 85.3) that survived to weaning compared to those of the starch treatment group. Sow feed intake and weight gain during lactation were not affected by dietary treatment.

In a second experiment, the addition of 1,3-Butanediol to the diet of sows during late gestation was shown to increase the metabolic stability of the newborn pig by increasing the level of liver glycogen present in the pig at birth and delaying the onset of hypoglycemia in pigs which were allowed to nurse or were fasted from birth to 12 hr of age (table 4). In addition, the colostrum of sows fed 1,3-Butanediol contained a higher percent fat than that of sows fed the control diet (table 5).

TABLE 4

Effect on 1,3-Butanediol Supplementation in Sows During Late Gestation on Plasma Glucose and Liver Glycogen Stores in Neonatal Pigs.[a]

| Age of Pig, hr | Feeding Regime | Prepartum Treatment[a] | |
|---|---|---|---|
| | | Control | 1,3-Butanediol |
| | | Liver glycogen, mg | |
| 0 | — | 3.47 | 4.30 |
| 12 | Nursed | .70 | .85 |
| 12 | Fasted | .48 | .96 |
| | | Blood glucose, mg/dl | |
| 0 | — | 137.6 | 128.7 |
| 12 | Nursed | 92.7 | 124.2 |
| 12 | Fasted | 84.7 | 93.8 |

[a]Thirty and 42 pigs represented in the control and 1,3-Butanediol treatments, respectively.

TABLE 5

Effect of 1,3-Butanediol Supplementation in Sows During Late Gestation on the Fat and Protein Content of Sow's Colostrum.[a]

| Hr Postpartum | Prepartum Treatment[a] | |
|---|---|---|
| | Control | 1,3-Butanediol |
| | Colostrum fat, % | |
| 0 | 2.7 | 4.3 |
| 12 | 3.1 | 3.9 |
| | Colostrum protein, % | |
| 0 | 13.8 | 15.1 |
| 12 | 10.5 | 10.5 |

[a]Ten and fourteen sows represented in the control and 1,3-Butanediol treatments, respectively.

What is claimed:

1. A method of treating a pregnant sow to improve the metabolic stability of newborn pigs and to increase the survival rate of said newborn pigs which comprise administering to the pregnant sow during its late stages of gestation an effective amount of a material selected from the group consisting of a dihydroxy alkanol having 3 to 10 carbon atoms, a triglyceride of glycerol and fatty acids containing 8 to 12 carbon atoms and the mono- and diol esters of said alkanols and said fatty acids.

2. The method of claim 1 wherein the dihydroxy alkanol is 1,3-butanediol.

3. The method of claim 1 wherein the alkanol, the triglyceride or the diol ester of said alkanols and fatty acids are added as a food supplement to the sow's diet.

4. The method of claim 3 wherein the alkanol, the triglyceride or the diol ester of said alkanols and fatty acids are added in an amount sufficient to provide about 6 to 20% of the dietary energy in the sow's diet.

5. The method of claim 1 wherein the alkanol, the triglyceride and the diol esters of said alkanols and fatty acids are administered about 4 to 12 days before parturition and continued until parturition.

6. The method of claim 1 wherein the diester is 1,3-butanediol monooctanoate.

* * * * *